(12) United States Patent
Depenbusch

(10) Patent No.: US 12,383,250 B2
(45) Date of Patent: Aug. 12, 2025

(54) DEVICES FOR INTRAOCULAR SURGERY

(71) Applicant: Michael Jerome Designs, LLC, Chandler, AZ (US)

(72) Inventor: Michael Jerome Depenbusch, Chandler, AZ (US)

(73) Assignee: Michael Jerome Designs, LLC, Chandler, AZ (US)

( * ) Notice: Subject to any disclaimer, the term of this patent is extended or adjusted under 35 U.S.C. 154(b) by 680 days.

(21) Appl. No.: 17/510,070

(22) Filed: Oct. 25, 2021

(65) Prior Publication Data

US 2022/0039787 A1  Feb. 10, 2022

Related U.S. Application Data

(63) Continuation of application No. 16/338,418, filed as application No. PCT/US2017/055797 on Oct. 9, 2017, now Pat. No. 11,179,147.
(Continued)

(51) Int. Cl.
*A61B 17/02* (2006.01)
*A61B 17/00* (2006.01)
(Continued)

(52) U.S. Cl.
CPC ...... *A61B 17/0231* (2013.01); *A61F 9/00745* (2013.01); *A61M 3/0266* (2013.01);
(Continued)

(58) Field of Classification Search
CPC ............. A61B 17/0231; A61B 17/02; A61B 2217/007; A61B 2017/00876; A61B 17/0293; A61B 17/0281
See application file for complete search history.

(56) References Cited

U.S. PATENT DOCUMENTS 6,155,975 A    12/2000  Urich et al.
6,203,513 B1   3/2001   Yaron et al.
(Continued)

FOREIGN PATENT DOCUMENTS

WO    WO 2010/080356 A1    7/2010

OTHER PUBLICATIONS

PCT International Search Report and Written Opinion, PCT Application No. PCT/US2017/055797, Jan. 25, 2018, 16 pages.
(Continued)

*Primary Examiner* — Eduardo C Robert
*Assistant Examiner* — Holly Joanna Lane
(74) *Attorney, Agent, or Firm* — Fenwick & West LLP

(57) ABSTRACT

An anterior chamber maintainer (ACM) is fastened to the cornea of a patient's eye at one or more, or potentially two or more, points of contact. The ACM can be inserted through a first and second incision. The ACM can be fastened to each of the two incisions using, for example, friction surfaces, ridges, a malleable tip, magnets, a segmented tip, or other types of fasteners. The ACM includes openings to provide irrigation solution to maintain the volume of the patient's eye during cataract surgery. The shape of the openings can be customized to reduce the amount of turbulence caused by the irrigation solution. By fastening the ACM to the cornea, the ACM is less likely to shift around or become dislodged from the eye during surgery. The ACM can be integrated with iris retractors to hold the position of a floppy iris during surgery.

17 Claims, 12 Drawing Sheets

Related U.S. Application Data

(60) Provisional application No. 62/408,640, filed on Oct. 14, 2016, provisional application No. 62/408,643, filed on Oct. 14, 2016.

(51) Int. Cl.
*A61F 9/007* (2006.01)
*A61M 3/02* (2006.01)

(52) U.S. Cl.
CPC ............ *A61B 2017/00876* (2013.01); *A61B 2217/007* (2013.01); *A61M 2210/0612* (2013.01)

(56) References Cited

U.S. PATENT DOCUMENTS

| | | | | |
|---|---|---|---|---|
| 10,159,600 | B2* | 12/2018 | Horvath | A61F 9/00781 |
| 11,197,779 | B2* | 12/2021 | Van Meter | A61B 3/16 |
| 2004/0111050 | A1* | 6/2004 | Smedley | A61F 9/00781 |
| | | | | 604/9 |
| 2004/0127843 | A1* | 7/2004 | Tu | A61F 9/0017 |
| | | | | 604/27 |
| 2007/0118147 | A1* | 5/2007 | Smedley | A61F 9/0017 |
| | | | | 606/107 |
| 2007/0191863 | A1* | 8/2007 | De Juan | A61F 9/007 |
| | | | | 606/108 |
| 2009/0182421 | A1 | 7/2009 | Silvestrini et al. | |
| 2010/0274259 | A1 | 10/2010 | Yaron et al. | |
| 2010/0280435 | A1 | 11/2010 | Raney et al. | |
| 2013/0215383 | A1 | 8/2013 | Siminou | |
| 2014/0074011 | A1 | 3/2014 | Charles | |
| 2014/0107428 | A1* | 4/2014 | LaConte | A61B 3/117 |
| | | | | 600/249 |
| 2014/0163455 | A1 | 6/2014 | Wilson et al. | |
| 2015/0148729 | A1* | 5/2015 | Pinchuk | A61M 27/002 |
| | | | | 604/8 |
| 2017/0007451 | A1* | 1/2017 | Depenbusch | A61M 1/85 |
| 2019/0209374 | A1* | 7/2019 | Banko | A61F 9/00745 |

OTHER PUBLICATIONS

United States Office Action, U.S. Appl. No. 16/338,418, filed Apr. 22, 2021, eight pages.
United States Office Action, U.S. Appl. No. 16/338,418, filed Oct. 20, 2020, 11 pages.

* cited by examiner

200

```
┌─────────────────────────────────────────────────────┐
│ Cut a first incision and a second incision in a cornea of an eye. │
│                         202                         │
└─────────────────────────────────────────────────────┘
                            │
                            ▼
┌─────────────────────────────────────────────────────┐
│           Insert an ACM through the first incision.           │
│                         204                         │
└─────────────────────────────────────────────────────┘
                            │
                            ▼
┌─────────────────────────────────────────────────────┐
│          Insert the ACM through the second incision.          │
│                         206                         │
└─────────────────────────────────────────────────────┘
                            │
                            ▼
┌─────────────────────────────────────────────────────┐
│              Fasten the ACM to the second incision.              │
│                         208                         │
└─────────────────────────────────────────────────────┘
```

```
Cut a first incision and a second incision in a cornea of an eye.
302
          │
          ▼
Insert an ACM with a needle through the first incision.
304
          │
          ▼
Insert the ACM through the second incision.
306
          │
          ▼
Fasten the ACM to the second incision.
308
          │
          ▼
Remove the needle from the ACM.
310
```

FIG. 3A

DEVICES FOR INTRAOCULAR SURGERY

CROSS-REFERENCE TO RELATED APPLICATIONS

This application is a continuation of U.S. application Ser. No. 16/338,418, filed Mar. 29, 2019, which is a 35 U.S.C. 371 national stage filing of International Application No. PCT/US2017/055797, filed on Oct. 9, 2017, which claims the benefit of and priority to U.S. Provisional Application No. 62/408,643, filed Oct. 14, 2016, and U.S. Provisional Application No. 62/408,640, filed Oct. 14, 2016, all of which are incorporated by reference herein in their entirety.

BACKGROUND

Field of Art

This invention relates generally to the field of ocular surgery, and particularly to an anterior chamber maintainer and fluidic control system for surgery.

Description of the Related Art

The anterior segment of the human eye includes the cornea, iris, and lens. A patient with an eye disease or disorder may require anterior segment surgery, for example, cataract surgery. Cataract surgery involves removing the lens of a patient's eye that has become cloudy due to cataract formation, and replacing the lens with a clear artificial lens. A physician begins by making incisions in the eye to facilitate the insertion of surgical instruments. The physician uses surgical instruments such as choppers to break a cataract into smaller fragments so that a vacuum can aspirate the fragments to remove them from the eye via an incision. Once the fragments are removed, the physician inserts the artificial lens through an incision. Phacoemulsification is a type of cataract surgical procedure that uses ultrasound to emulsify the cataract. In particular, a physician inserts a phacoemulsification tip to the location of the cataract, and the phacoemulsification tip vibrates at an ultrasonic frequency to break down the cataract. The phacoemulsification tip includes a lumen (a hollow cavity) such that cataract fragments can be vacuumed out of the eye through the phacoemulsification tip. Phacoemulsification can also be completed without ultrasound using a phacoemulsification tip by mechanically breaking up the cataract, such as with an instrument called a chopper, and aspirating through the tip.

Existing phacoemulsification tips and other types of aspiration tips can also serve as an anterior chamber maintainer (ACM). An anterior chamber maintainer provides an irrigation solution at a certain pressure into the eye to maintain intraocular pressure (e.g., to maintain the anterior chamber shape of the eye) and cool the phacoemulsification tip during surgery. When a physician is aspirating fragments from the eye, irrigation solution at a higher pressure should be provided into the eye to help flush out the fragments (as well as to maintain the anterior chamber shape). Existing solutions provide solution at a single pressure level. For example, the solution is provided from a bottle positioned at a particular height. To change the pressure level, existing solutions require significant pause during surgery since the physician, nurse, or a technician needs to manually change settings of the system to reposition the bottle. However, during the surgery (e.g., a 5-20 minute procedure), the physician may need to quickly change between a low pressure solution and a high pressure solution, which is not possible in the time that it takes to manually reposition the bottle.

Existing anterior chamber maintainers are inserted into the eye through an incision in the cornea. Existing anterior chamber maintainers are difficult to stabilize in a fixed position and may also become dislodged from the eye during surgery. Further, due to the positioning of the anterior chamber maintainer, the irrigation solution can cause turbulence and fluid whirlpools that disrupts the physician performing the surgery. It is desirable and challenging to fasten an anterior chamber maintainer inside a patient's eye and provide the irrigation solution without causing turbulence and/or without causing the anterior chamber maintainer to become dislodged.

SUMMARY

In an embodiment, an anterior chamber maintainer (ACM) is fastened to the cornea of a patient's eye at one or more, or potentially two or more, points of contact. The ACM can be inserted through a first incision and a second incision. The ACM can be fastened to each of the two incisions using, for example, friction surfaces, ridges, a malleable tip, magnets, a segmented tip, or other types of fasteners. The ACM includes openings to provide irrigation solution (e.g., a fluid) to maintain the volume of the patient's eye during cataract surgery. The shape of the openings can be customized to reduce the amount of turbulence caused by the irrigation solution. By fastening the ACM to the cornea, the ACM is less likely to shift around or become dislodged from the eye during surgery. The ACM can be integrated with iris retractors to enlarge the pupil and to hold the position of a floppy iris during surgery. Further, fastening the ACM to multiple points of contact on the eye enables the ACM to direct the flow of irrigation solution in certain directions.

In various embodiments, an anterior chamber maintainer (ACM) includes an exterior wall and an interior wall forming a tubular structure. The tubular structure includes a first section including a first fastener configured to be fastened to a first location of a cornea of an eye, a second section including a second fastener configured to be fastened to a second location of the cornea, and a third section adjacent to the first section and the second section. The third section includes one or more openings configured to deliver fluid from a lumen, formed by the interior wall, into the eye. The ACM further includes a sharp edge positioned in the vicinity of the first section.

In one or more embodiments, the one or more openings includes a plurality of openings each having a different size.

In one or more embodiments, the one or more openings includes a first opening configured to direct the fluid in a direction into the eye, and a second opening configured to direct the fluid in a different direction into the eye.

In one or more embodiments, the third section further includes one or more iris retractors configured to be fastened to a portion of an iris tissue of the eye.

In one or more embodiments, at least one of the first fastener and the second fastener is a friction surface having a higher coefficient of friction than another coefficient of friction of a surface of the third section.

In one or more embodiments, at least one of the first fastener and the second fastener is a plurality of ridges that physically contacts the first location or the second location.

In one or more embodiments, at least one of the first fastener and the second fastener is a malleable tip.

In one or more embodiments, at least one of the first fastener and the second fastener is a magnet.

In one or more embodiments, the anterior chamber maintainer is coupled to a fluidic control system to receive the fluid at one of a plurality of different fluid pressures.

In one or more embodiments, the third section includes a first curved segment adjacent to the first section and a second curved segment adjacent to the second section.

In an embodiment, a fluidic control system includes at least two containers of fluid positioned at different heights. Alternatively, the system includes a container with two or more chambers each having different compression levels such as a low and a high compression. A physician can use the fluidic control system during cataract surgery (or other ocular surgeries) to provide solutions, corresponding to two different pressures (e.g., fluid pressures), into a patient's eye. A low pressure (lower height) solution can be used to maintain the eye's intraocular pressure, while a high pressure (higher height) solution can be used when the physician is aspirating fragments from the eye during surgery. The physician can use pedals or other input devices to control the delivery of the fluid. For example, the physician adjusts the pedal to a first position to deliver solution from one container and adjusts the pedal to a second position to deliver solution from another container.

In various embodiments, a method for using an anterior chamber maintainer includes cutting a first incision and a second incision in a cornea of an eye. The method further includes inserting the anterior chamber maintainer through the first incision, the anterior chamber maintainer being a tubular structure and including one or more openings along a longitudinal body of the anterior chamber maintainer. The method further includes inserting the anterior chamber maintainer through the second incision such that the one or more openings are positioned inside the eye. The method further includes fastening the anterior chamber maintainer to the first incision and the second incision. The method further includes providing fluid into the eye using the one or more openings of the anterior chamber maintainer.

In one or more embodiments, the method further includes fastening one or more iris retractors of the anterior chamber maintainer to a portion of an iris tissue of the eye.

In one or more embodiments, the method further includes manipulating another tool in the eye while the providing the fluid into the eye using the one or more openings of the anterior chamber maintainer.

In one or more embodiments, fastening the anterior chamber maintainer includes inserting another tool into the eye and manipulating the tool to position the anterior chamber maintainer.

In one or more embodiments, inserting the anterior chamber maintainer through the first incision includes inserting a needle through the first incision, where the needle positioned inside the tubular structure of the anterior chamber maintainer. The method further includes removing the needle from the tubular structure of the anterior chamber maintainer.

In one or more embodiments, the method further includes cutting a third incision in the cornea of an eye, and fastening the anterior chamber maintainer to the third incision.

In various embodiments, a system includes a stand coupled to a first container having a first compression level and a second container having a second compression level different than the first compression level. The system further includes a pedal including a lever. The system further includes an interface coupled to the pedal, the first container, and the second container. The interface is configured to provide first fluid from the first container in response to determining that the lever is at a first position and provide second fluid from the second container in response to determining that the lever is at a second position.

In one or more embodiments, the first container and the second container are positioned at different heights from each other on the stand.

In one or more embodiments, the system further includes an anterior chamber maintainer coupled to the interface and configured to receive the first fluid and the second fluid.

In one or more embodiments, the system further includes an alignment device for aligning a reference point of the stand to a patient receiving at least one of the first fluid and the second fluid.

BRIEF DESCRIPTION OF DRAWINGS

FIG. 2A is a flowchart of a process of fastening an anterior chamber maintainer to an eye according to one embodiment.

FIG. 3A is another flowchart of a process of fastening an anterior chamber maintainer to an eye according to one embodiment.

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Particular embodiments as described herein relate to phacoemulsification tips, which may also be referred to as phaco tips, phacoemulsification probes, phaco probes, phacoemulsification needles, phaco needles, vacuum tips, or aspiration tips. The fragments of cataracts or fragments of other anatomical tissues (e.g., corneal tissue) that are produced during a surgical procedure are referred to as fragments herein. A physician may conduct a surgery with the help of nurses or other types of assistants. For simplicity, each of these individuals may be referred to herein as a physician.

The figures are not necessarily drawn to scale. In particular, certain features of anterior chamber maintainers (ACM), fluidic control system, other surgical tools, or parts of the eye have been enlarged for purposes of illustration and clarity. The ACMs described herein can be connected to a source of irrigation solution and a pump (e.g., a fluidic control system) to transfer the irrigation solution into the eye. Further, the phaco tips described herein can be connected to a pump or other systems (e.g., a fluidic control system) used to create vacuum or suction in the phaco tips to aspirate fragments from a patient's eye.

Example Prior Art

Figure 1A:
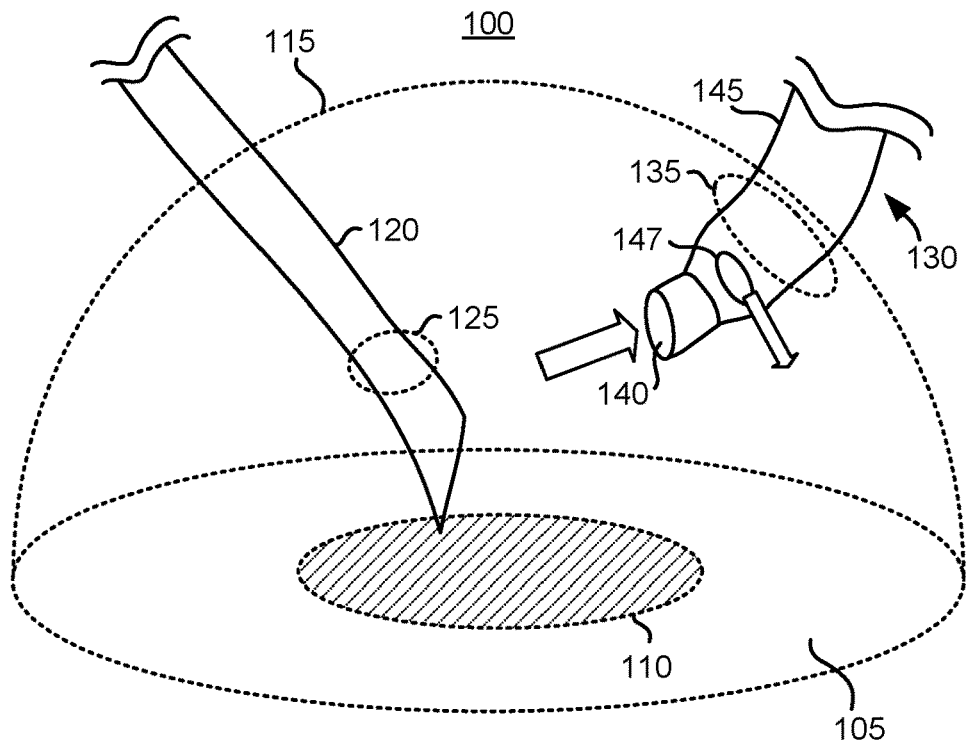
FIG. 1A shows a prior art phacoemulsification tip.

FIG. 1A shows a prior art phacoemulsification tip 130. A physician can use the phaco tip 130 during cataract surgery to provide an irrigation solution, e.g., a balanced salt solution (BSS), into an eye 100 of a patient. A lumen 140 of the phaco tip 130 is surrounded by a sleeve 145. The irrigation solution (e.g., a fluid) enters a hand piece (not shown in FIG. 1A) coupled to the phaco tip 130 and then travels into the sleeve 145 surrounding the phaco tip 130. The fluid then enters the eye 100 through a port 147 in the sleeve 145 to maintain intraocular pressure and cool the phaco tip 130 (e.g., functioning as a heat sink). Maintaining intraocular pressure is required to maintain the anterior chamber shape of the eye 100 (thus preventing the eye from collapsing) during surgery. The heat generated by ultrasound of the phaco tip 130 during phacoemulsification can burn surrounding tissue of the eye 100 if the phaco tip 130 is not cooled using the irrigation solution or using another cooling method.

During a typical cataract surgery, a physician (e.g., a surgeon) cuts an incision 135 in the cornea 115 of the eye 100. The physician inserts the phaco tip 130 with an irrigation sleeve into the eye 100 through the incision 135. Since the phaco tip 130 and the irrigation sleeve are coupled to the eye 100 only at the interface of the incision 135 and held by the physician by a hand piece and manipulated as a tool, the phaco tip 130 may not remain in a stable position during surgery. Since the physician will be moving the phaco tip 130 to different positions in the eye 100, there may be turbulence and unpredictable fluidics inside the eye 100. Other disadvantages of providing irrigation solution through a sleeve of a phaco tip include variations in the fluid flow due to variations in the size or geometry of the phaco tip and/or sleeve, and a high likelihood of causing the anterior chamber of the eye to collapse during surgery. Additionally, the irrigation solution flowing out of the sleeve 145 can interfere with fragments being vacuumed into the lumen 140, e.g., because the irrigation solution and fragments are trying to travel in opposing directions. Existing phaco tips can require up to 4 millimeters of clearance into the eye, e.g., the phaco tip 130 needs to be inserted approximately 4 millimeters through the incision 135. Since the cornea 115 of humans has an average diameter of 11-12 millimeters, a 4 millimeter clearance can make it difficult for the phaco tip 130 to direct irrigation solution in tight corners inside the eye 100. In addition, if the sleeve 145 becomes pulled into a wound of the eye 100, the phaco tip 130 may overhydrate the wound with irrigation solution, which would interfere with maintaining the intraocular pressure.

During cataract surgery, the physician can use additional surgical tools such as a chopper 120 to break a cataract into smaller fragments. The physician inserts the chopper 120 via another incision 125 in the cornea 115. The physician uses the chopper 120 to reach cataracts, which are located at the lens of the eye 100. The lens of the eye 100 is behind the pupil 110, which is the opening formed by the iris 105 tissue of the eye 100. Phaco tips may also be used in other types of surgical procedures.

Figure 1B:
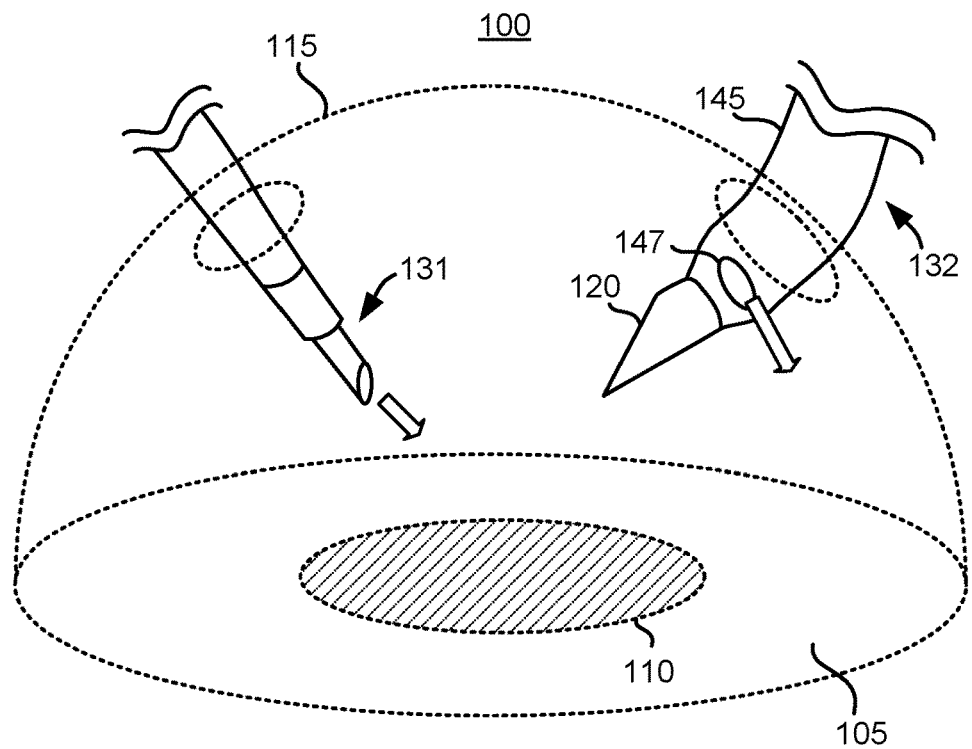
FIG. 1B shows a prior art anterior chamber maintainer.

FIG. 1B shows a prior art anterior chamber maintainer 131. The ACM 131 is a tube that includes a lumen and an opening at the distal end of the tube to provide irrigation solution into the eye 100. The physician inserts the ACM 131 into the eye 100 through an incision in the cornea 115. A physician may have difficulty manually maintaining a stable position of the ACM 131. The ACM 131 frequently becomes dislodged unexpectedly during surgery because the ACM 131 is not securely fastened to the eye 100. This "typical" ACM is not stable and the tip of the ACM can damage surrounding tissue (e.g. cornea, iris, or lens). The instability of the positioning of the "typical" ACM also causes the fluidics in the eye to be unpredictable.

FIG. 1B also shows another prior art phaco tip 132. Similar to the phaco tip 130 shown in FIG. 1A, the phaco tip 132 can also provide irrigation solution into the eye 100 through the port 147 of the sleeve 145. Similar to the ACM 131, the phaco tip 132 may also become dislodged unexpectedly during surgery because the phaco tip 132 is not securely fastened to the eye 100.

Example Double Fastening an Anterior Chamber Maintainer

Figure 2B:
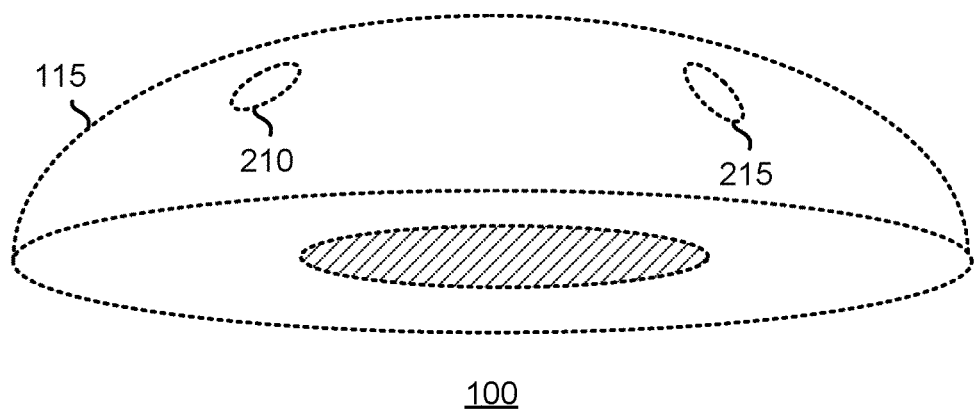
FIG. 2B shows incisions cut into a cornea of an eye according to one embodiment.

FIG. 2A is a flowchart of a process 200 of fastening an anterior chamber maintainer to an eye according to one embodiment. The process 200 may be performed by one or more physicians, a surgical robotic system, or any combination thereof. The process 200 may include different or additional steps than those described in conjunction with FIG. 2A in some embodiments or perform steps in different orders than the order described in conjunction with FIG. 2A. The process 200 is explained below with reference to FIGS. 2B-D.

FIG. 2B shows incisions cut into a cornea 115 of an eye 100 according to one embodiment. The physician (or a surgical robotic system) cuts 202 a first incision 215 and a second incision 210 into the cornea 115 of the eye 100. These can be incisions made with a scalpel or another instrument, or can be incisions made with a tip of the ACM itself as it is being inserted into the cornea 115 if the ACM has a sharp tip or has a removable attachment to the tip that is sharp.

Figure 2C:
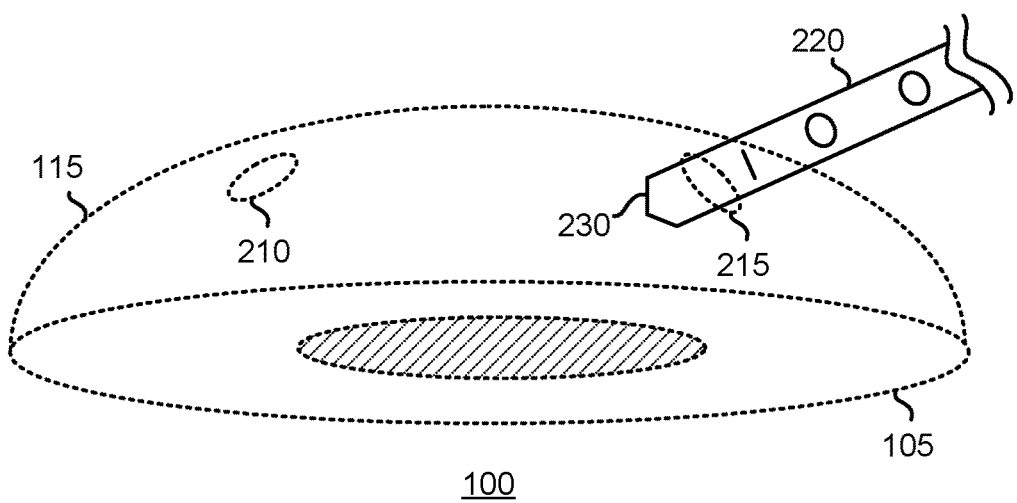
FIG. 2C shows an anterior chamber maintainer inserted into the eye shown in FIG. 2B according to one embodiment.

FIG. 2C shows an ACM 220 inserted into the eye 100 shown in FIG. 2B according to one embodiment. The physician inserts 204 the ACM 220 through the first incision 215. The ACM 220 can have a sharp tip 230 to facilitate insertion through the first incision 215.

Figure 2D:
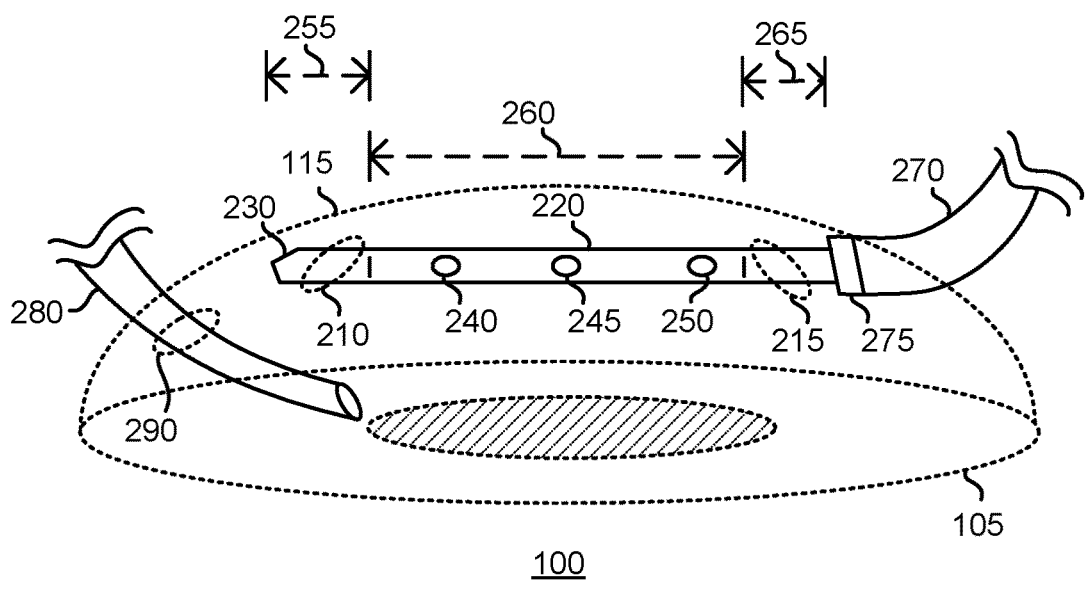
FIG. 2D shows the anterior chamber maintainer shown in FIG. 2C fastened to the eye according to one embodiment.

FIG. 2D shows the ACM 220 shown in FIG. 2C fastened to the eye 100 according to one embodiment. The physician inserts 206 the ACM 220 through the second incision 210. The physician fastens 208 the ACM 220 to the second incision 210. In some embodiments, the physician also fastens the ACM 220 to the first incision 215.

The ACM 220 includes one or more openings to provide irrigation solution into the eye 100 once the ACM 220 is fastened to the eye 100. In the embodiment shown in FIG. 2D, the ACM 220 includes three openings 240, 245, and 250. The openings are located within the cornea 115 such that irrigation solution is not leaked outside of the eye 100. In one embodiment, the length 260 of the ACM 220 located inside the cornea 115 is approximately 6 millimeters to 9 millimeters. In one embodiment, the lengths 255 and 265 of the ACM 220 that are each located outside of the cornea 115 after the ACM 220 has been fastened are approximately 3 millimeters to 6 millimeters. In other embodiments, the ACM 220 may have a different length located inside the cornea 115 and/or different lengths located outside of the cornea 115. In one embodiment, the length 260 is 9 millimeters and the lengths 255 and 265 are each 3 millimeters, so the total length of the ACM 220 is 15 millimeters. The ACM 220 can include visual markers to indicate the length 260, e.g., to assist the physician while inserting the ACM 220 into the eye 100. The ACM 220 is coupled to an infusion line 270 by a port 275. The infusion line 270 provides the irrigation solution from an irrigation solution source (not shown in FIG. 2D) to the ACM 220. For example, the irrigation solution source may be a fluidic control system, further described below with reference to FIG. 9. Fastening the ACM 220 to the eye 100 may stabilize the movement of contents (e.g., cataract fragments and irrigation solution) inside the anterior chamber, and thus reduce the likelihood that the posterior capsule of the eye will rupture during surgery.

The physician can cut another incision 290 in the cornea 115 to insert additional surgical tools during the surgery. For example, the physician inserts a phaco tip 280 through the incision 290 to operate in the eye 100. In one embodiment, the phaco tip 280 is designed to be used without application of ultrasound or laser energy to the eye, such as the phaco tips described in U.S. patent application Ser. No. 15/196,844, filed on Jun. 29, 2016, which is hereby incorporated by reference herein in its entirety. In some embodiments, regardless of whether the phaco tip 280 uses ultrasound, the phaco tip 280 may not require a sleeve for liquid cooling using the irrigation solution. Thus, the irrigation solution can be provided by a separate ACM tool (e.g., the ACM 220).

Figure 3B:
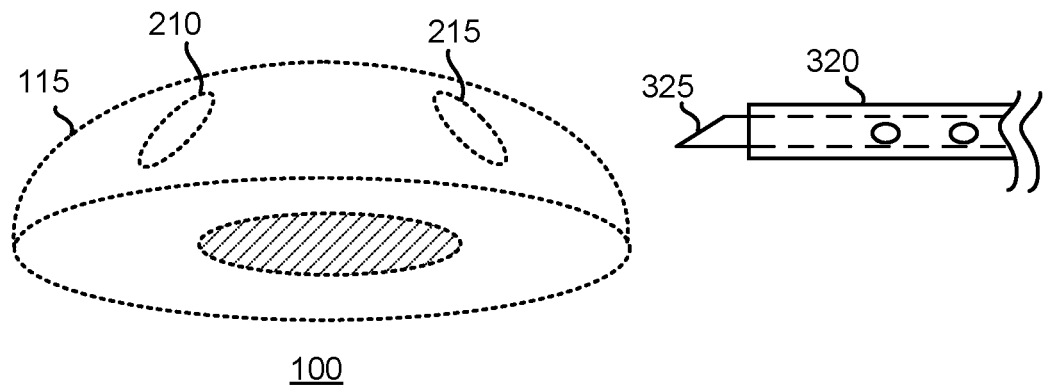
FIG. 3B shows an anterior chamber maintainer with a needle according to one embodiment.

FIG. 3A is another flowchart of a process 300 of fastening an anterior chamber maintainer to an eye according to one embodiment. The process 300 may be performed by one or more physicians, a surgical robotic system, or any combination thereof. The process 300 may include different or additional steps than those described in conjunction with FIG. 3A in some embodiments or perform steps in different orders than the order described in conjunction with FIG. 3A. The process 300 is explained below with reference to FIGS. 3B-D.

FIG. 3B shows an anterior chamber maintainer 320 with a needle 325 according to one embodiment. The physician cuts 302 a first incision 215 and a second incision 210 into the cornea 115 of the eye 100.

Figure 3C:
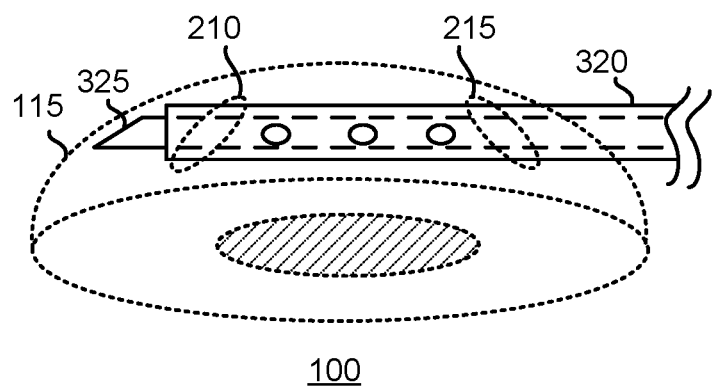
FIG. 3C shows the anterior chamber maintainer shown in FIG. 3B inserted into an eye according to one embodiment.

FIG. 3C shows the ACM 320 shown in FIG. 3B inserted into an eye according to one embodiment. The physician inserts 304 the ACM 320 with the needle 325 through the first incision 215. The needle 325 has a smaller radius than the ACM 320 and is positioned inside the ACM 320, e.g., the needle 325 can slide within the lumen of the ACM 320. In another embodiment, the needle 325 has a slightly larger radius than the ACM 320 and fits over the ACM 320 like a sleeve that can be withdrawn after insertion of the ACM 320. Since the needle 325 has a sharp tip, the tip of the ACM 320 does not necessarily require a sharp tip to facilitate insertion of the ACM 320 through incisions in the cornea 115. The physician inserts 306 the ACM 320 through the second incision 210. The physician fastens 308 the ACM 320 to the second incision 210.

Figure 3D:
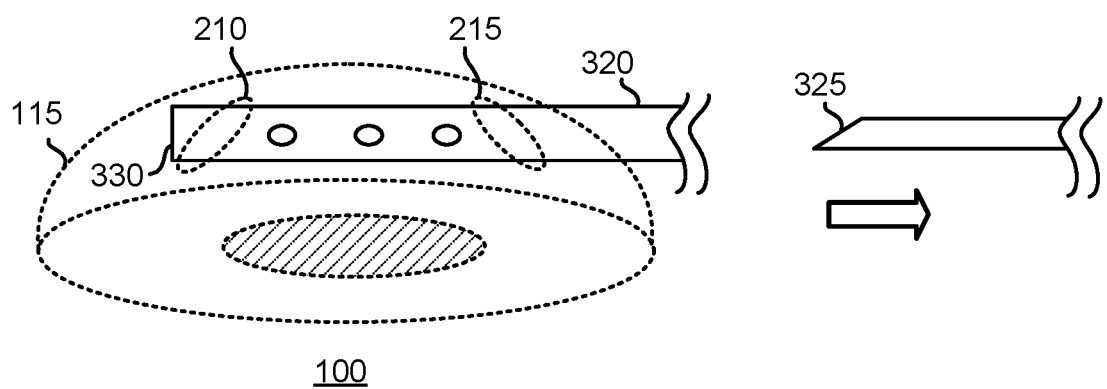
FIG. 3D shows the anterior chamber maintainer shown in FIG. 3C with the needle removed according to one embodiment.

FIG. 3D shows the ACM 320 shown in FIG. 3C with the needle 325 removed according to one embodiment. The physician removes 310 the needle 325 from the ACM 320, while leaving the ACM 320 fastened to the cornea 115 at the first incision 215 and the second incision 210. The tip 330 of the ACM 320 forms a self-sealing waterproof seal after the needle 325 removed to prevent irrigation solution from leaking outside of the eye 100.

Example Anterior Chamber Maintainer Openings for Fluid Flow

Figure 4A:
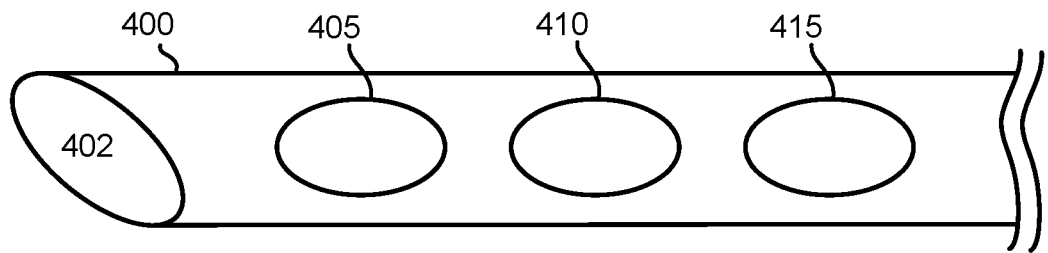
FIG. 4A shows an anterior chamber maintainer with constant sized openings according to one embodiment.

FIG. 4A shows an anterior chamber maintainer 400 with constant sized openings according to one embodiment. The ACM 400 includes three openings 405, 410, and 415. Each opening is the same size, and approximately 0.3 millimeters to 1.5 millimeters in length in one embodiment. Though the openings shown in FIG. 4A are ellipsoid, in other embodiments, the openings can have other types of shapes, e.g., rectangular, a shape with both straight and curved edges, etc. The openings of the ACM 400 are located along the longitudinal body of the ACM 400. Since there is more surface area along the longitudinal body, the ACM 400 can facilitate larger sized openings compared to the ACM 130, which can be advantageous to increase the throughput of irrigation solution. In some embodiments, the distal tip of the ACM 400 is sealed. In other embodiments, the distal tip of the ACM 400 also includes an opening. The opening at the distal tip of the ACM 400 can be waterproof sealed.

The ACM 400 has an ellipsoid shaped cross sectional area 402, e.g., a circular or oval shaped cross sectional area. In one embodiment with a circular cross sectional area 402, the inner diameter (of an inner wall) of the ACM 400 is approximately 0.84 millimeters, and the outer diameter (of an outer wall) of the ACM 400 is approximately 1.27 millimeters. In other embodiments, the inner and outer diameters of the ACM 400 may be different sizes, and the cross sectional area may be a different shape. The inner wall of the ACM 400 forms a lumen through which irrigation solution flows through. In some embodiments, an oval shaped cross sectional area 402 is advantageous because the oval shape stabilizes the ACM 400 fastened to the eye 100. In particular, an ACM with an oval shaped cross sectional area is less likely to rotate along a longitudinal axis of the ACM, compared to another ACM with a circular shaped cross sectional area. In one embodiment, the minor axis of the oval shaped cross sectional area 402 is approximately 1.0 millimeters and the major axis of the oval shaped cross sectional area 402 is approximately 1.5 millimeters.

Figure 4B:
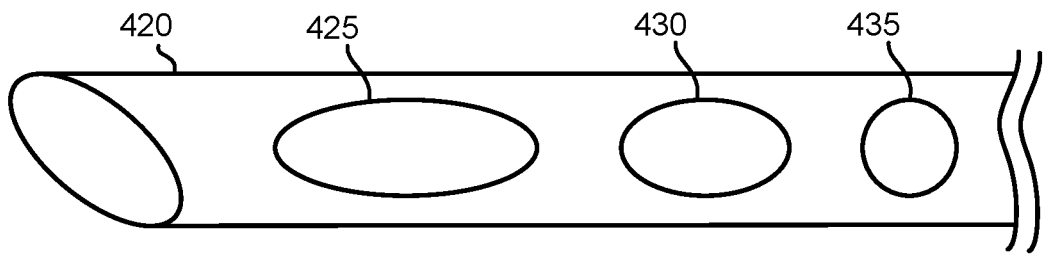
FIG. 4B shows an anterior chamber maintainer with variable sized openings according to one embodiment.

FIG. 4B shows an anterior chamber maintainer 420 with variable sized openings according to one embodiment. The ACM 420 includes a first opening 425 that has a length of approximately 1.5 millimeters, a second opening 430 of approximately 0.75 millimeters, and a third opening 435 of approximately 0.3 millimeters. The width of the openings 425, 430, and 435 are shown to be equal in FIG. 4B, though in other embodiments, the width of the openings are not necessarily equal. Openings with variable lengths can be advantageous, for example, because the openings provide more uniform flow of the irrigation solution. In particular, since the fluid pressure is greater toward the distal end of the ACM 420 (e.g., the end further away from the irrigation solution source), the openings toward the distal end are larger the openings toward the proximal end. Thus, irrigation solution flow from the openings can have a more uniform pressure per surface area across the length of the ACM 420.

Figure 4C:
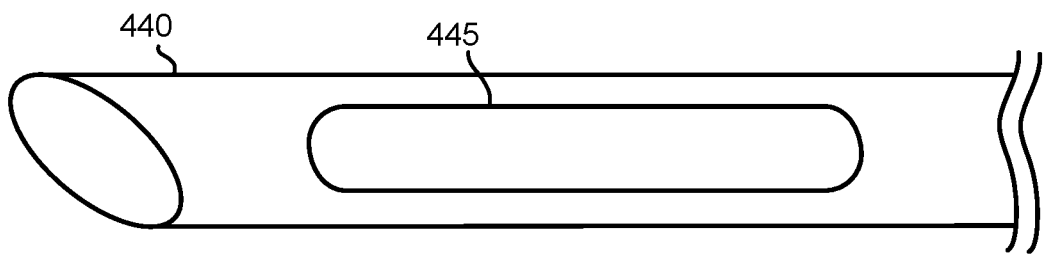
FIG. 4C shows an anterior chamber maintainer with a single opening according to one embodiment.

FIG. 4C shows an anterior chamber maintainer 440 with a single opening 445 according to one embodiment. In some embodiments, the single opening 445 is advantageous because the throughput of irrigation fluid from the single opening 445 is greater than the throughput of irrigation fluid from the multiple openings that are smaller in size.

Figure 4D:
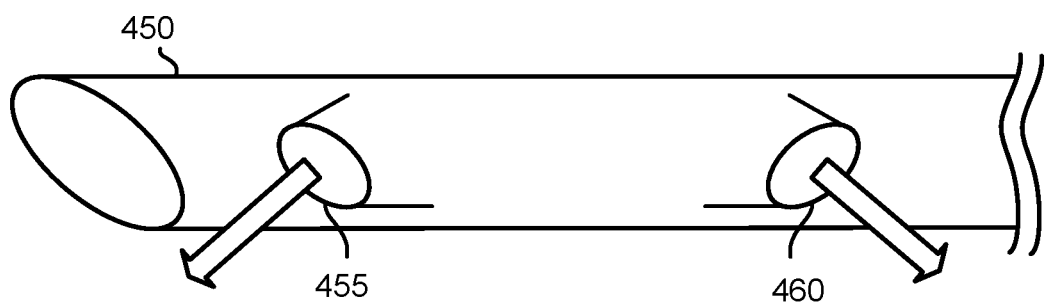
FIG. 4D shows an anterior chamber maintainer with openings that direct fluid flow according to one embodiment.

FIG. 4D shows an anterior chamber maintainer 450 with openings that direct fluid flow according to one embodiment. The ACM 450 includes a first opening 455 that directs the flow of irrigation solution toward the distal end of the ACM 450. The ACM 450 includes a second opening 460 that directs the flow of irrigation solution toward the proximal end of the ACM 450. In some embodiments, openings that direct fluid flow are advantageous because the direction of fluid flow can be designed to reduce the likelihood of causing turbulence in the eye 100. Further, the direction of fluid flow can be designed to be directed toward the operation site in the eye 100, e.g., the location of cataract fragments to be aspirated from the eye 100. The edges of the first and seconds openings may be sharp or dull and may be beveled or non-beveled. Though the first and seconds openings shown in FIG. 4D are funnel shaped, in other embodiments, the openings may have a different shape, e.g., cylindrical or a reverse-funnel shaped.

The various embodiments of openings in the anterior chamber maintainers shown in FIGS. 4A-D can be advantageous because the openings reduce or eliminate the likelihood that undesired turbulence or whirlpools occur inside the eye during surgery. In particular, the openings are designed to provide more control and uniform throughput of irrigation solution into the eye, compared to existing ACMs. Further, since the ACM is fastened to the cornea of the eye at two or more points (e.g., the first incision 215 and the second incision 210 shown in FIG. 2D and FIG. 3D), the ACM maintains a stable position and orientation in the eye while irrigation solution is provided via the openings. The ACM can be fastened to certain positions on the cornea to direct the flow of irrigation solution to an operative site, e.g., the location of cataracts to be aspirated from the eye.

Fastening the ACM to the cornea at two or more points can also provide support for the cornea to retain its shape and not collapse during surgery. The ACM can be fastened to the first incision 215 or the second incision 210 using a variety of types of fasteners, which are further described below in Section IV. Fasteners for Anterior Chamber Maintainers. Though not shown in FIGS. 4A-D, the ACM may be coupled (e.g., at a proximal end) to a fluidic control system (e.g., further described with respect to FIG. 9) to provide irrigation solution or other types of fluid to the ACM.

In some embodiments, one or more openings of an ACM facilitate aspiration of material from inside the eye. For example, the ACM is coupled to a vacuum pump (or syringe) and the ACM aspirates cataract fragments (or any other type of solid or viscoelastic material) from the eye through the openings. The vacuum force from the vacuum pump may attract cataract fragments to the openings, and/or a physician may feed cataract fragments to the openings, e.g., using a chopper. The ACM may include multiple openings and lumens for simultaneously providing irrigation solution and aspirating material. For example, a first set of openings is coupled to a first lumen coupled to source of irrigation solution, and a second set of openings is coupled to a second lumen coupled to a vacuum pump. In one embodiment, the ACM aspirates material using the openings and also includes a sleeve for providing the irrigation solution. An ACM fastened to the eye with integrated aspiration functionality is advantageous, for example, because the physician does not need to manually hold an aspiration device. Thus, the physician has a spare hand that can be used to hold or manipulate other surgical instruments.

Example Fasteners for Anterior Chamber Maintainers

Figure 5A:
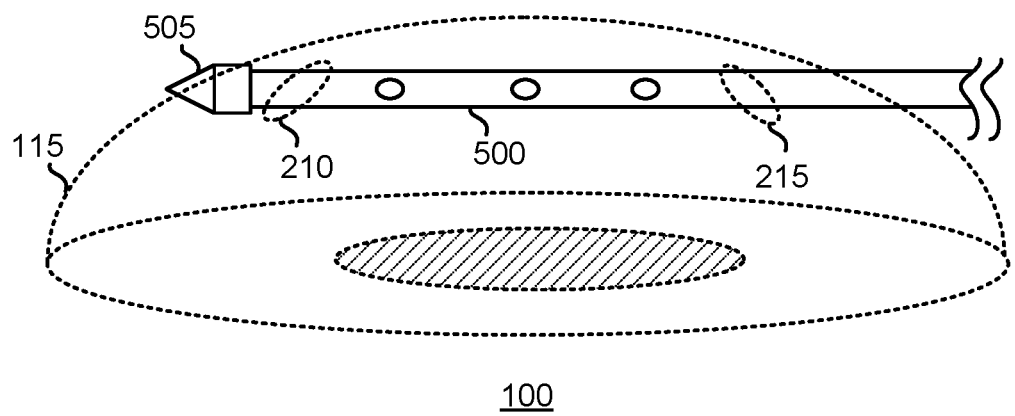
FIG. 5A shows an anterior chamber maintainer with a sharp tip fastened to an eye according to one embodiment.

FIG. 5A shows an anterior chamber maintainer 500 with a sharp tip 505 fastened to an eye 100 according to one embodiment. A physician can use the sharp tip 505 to insert the ACM 500 into the incisions 215 and 210 of the cornea 115. After inserting and fastening the ACM 500 to the cornea 115, the physician can detach the sharp tip 505 from the ACM 500 (e.g., exposing a distal tip of the ACM 500 that is not sharp). Detaching the sharp tip 505 can be advantageous because the sharp tip 505 will not interfere with the physician while the physician performs a surgery.

Figure 5B:
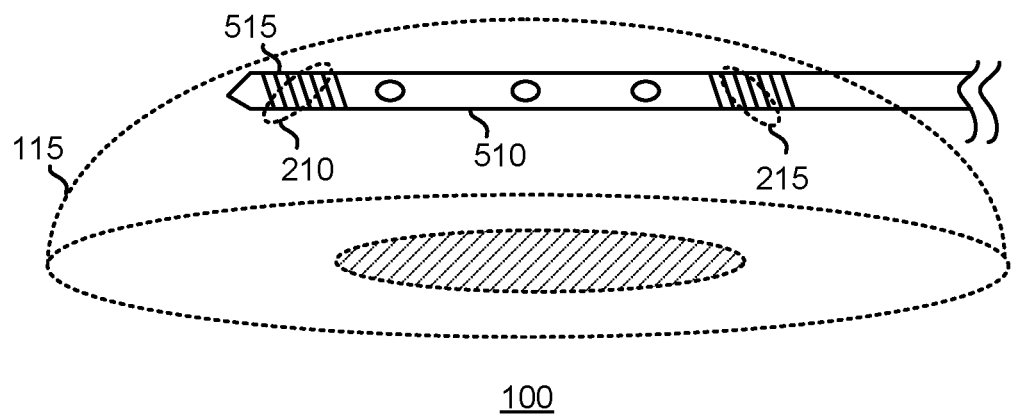
FIG. 5B shows an anterior chamber maintainer with friction surfaces fastened to an eye according to one embodiment.

FIG. 5B shows an anterior chamber maintainer 510 with friction surfaces fastened to an eye 100 according to one embodiment. The ACM 510 includes a friction surface 515 that physically contacts the second incision 210 when the ACM 510 is inserted and fastened to the cornea 115. The friction surface 515 can be a material with a higher coefficient of friction than that of the other surfaces of the ACM 510. The friction surface 515 can also be formed by grooves in the ACM 510. Thus, the friction surface 515 fastens the ACM 510 to the second incision 210. In some embodiments, the ACM 510 also includes another friction surface that physically contacts the first incision 215.

Figure 5C:
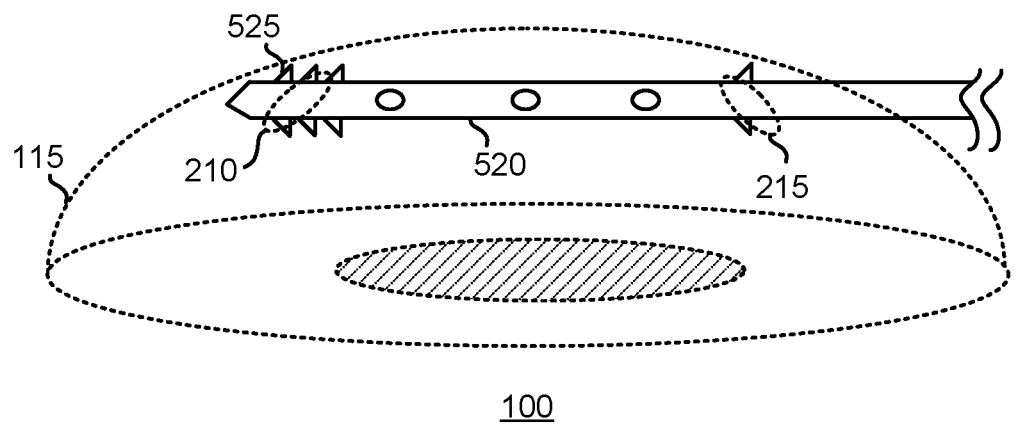
FIG. 5C shows an anterior chamber maintainer with ridges fastened to an eye according to one embodiment.

FIG. 5C shows an anterior chamber maintainer 520 with ridges 525 fastened to an eye 100 according to one embodiment. The ridges 525 physically contact the second incision 210 when the ACM 520 is inserted and fastened to the cornea 115. Thus, the ridges 525 fasten the ACM 520 to the second incision 210. Though the ridges 525 illustrated in FIG. 5C include multiple sets of triangular ridges, in other embodiments, the ACM 520 can include different types of ridges or different numbers of ridges. For example, the ridges can be rounded or rectangular-shaped. Triangular ridges can be advantageous because the triangular shape facilitates insertion of the ACM 520 into the cornea 115, but reduces the likelihood that the ACM 520 will become dislodged out of the cornea 115. In some embodiments, the ACM 520 also includes another ridge (or ridges) that physically contact the first incision 215. In some embodiments, the ridges are retractable such that the ridges can be retracted and flush with the outer surface of the ACM 520 during insertion into the cornea 115. Thus, the ACM 520 may experience less friction while being inserted into the cornea 115, and the ridges can be extended (from the retracted position) after insertion to fasten the ACM 520 in place.

Figure 5D:
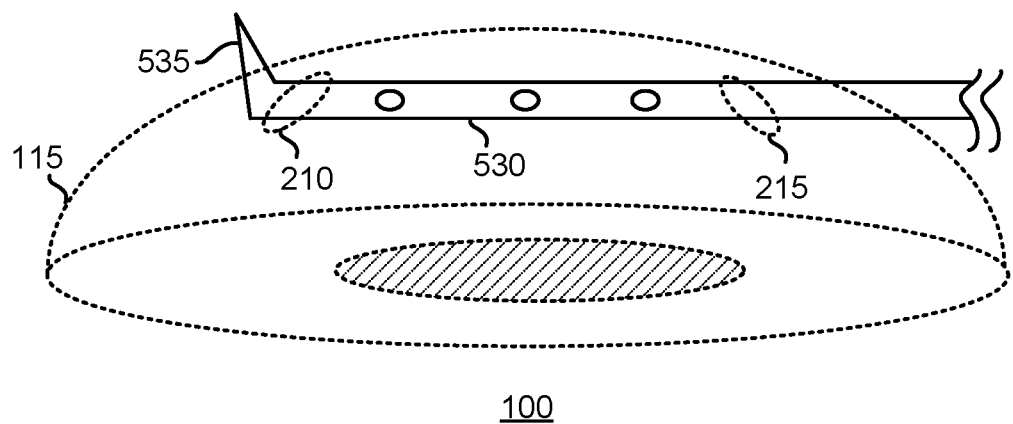
FIG. 5D shows an anterior chamber maintainer with a malleable tip fastened to an eye according to one embodiment.

FIG. 5D shows an anterior chamber maintainer 530 with a malleable tip 535 fastened to an eye 100 according to one embodiment. The physician bends the malleable tip 535 (e.g., using tweezers) after inserting the ACM 530 through the first incision 215 and second incision 210 in the cornea 115. Thus, the malleable tip 535 fastens the ACM 530 to the cornea 115. The malleable tip 535 can be sharp to facilitate insertion of the ACM 530 through the incisions.

Figure 5E:
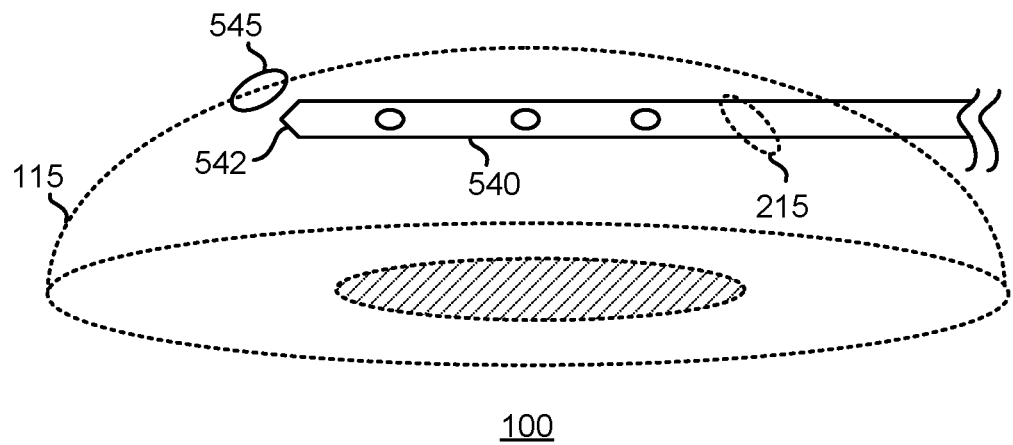
FIG. 5E shows an anterior chamber maintainer with a magnetic tip fastened to an eye according to one embodiment.

FIG. 5E shows an anterior chamber maintainer 540 with a magnetic tip 542 fastened to an eye 100 according to one embodiment. A physician can fasten the ACM 540 to the cornea 115 by positioning a magnet 545 on the cornea 115. In particular, the magnetic tip 542 is attracted by magnetic force to the magnet 545. The magnetic tip 542 can be sharp to facilitate insertion through the first incision 215. In some embodiments, fastening the ACM 540 to the cornea 115 using magnetic force is advantageous because the physician only needs to cut one incision in the cornea 115.

Figure 5F:
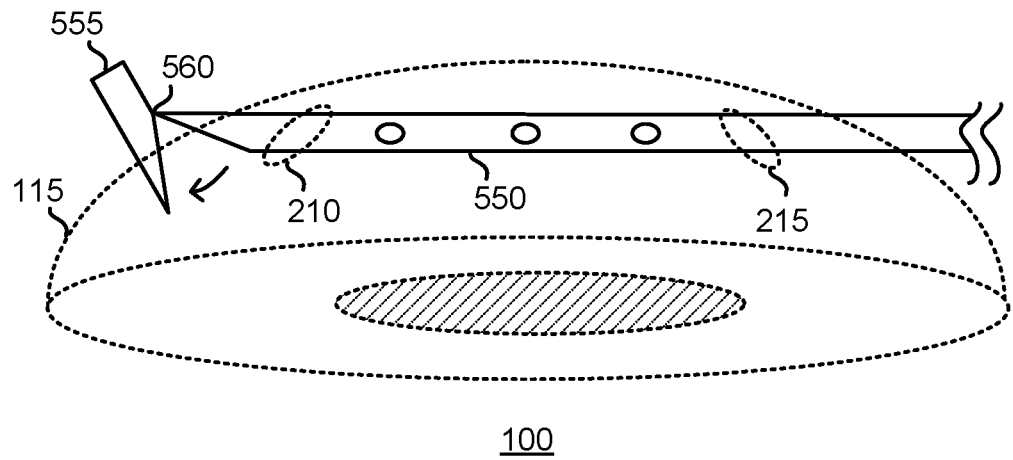
FIG. 5F shows an anterior chamber maintainer with a segmented tip fastened to an eye according to one embodiment.

FIG. 5F shows an anterior chamber maintainer 550 with a segmented tip 555 fastened to an eye 100 according to one embodiment. The physician folds out the segmented tip 555 (e.g., using tweezers) after inserting the ACM 550 through the first incision 215 and second incision 210 in the cornea 115. The segmented tip 555 is folded in alignment longitudinally with the ACM 550 during insertion into the cornea 115 and folds out by rotating about the pivot 560. Once the segmented tip 555 is folded out, the segmented tip 555 fastens the ACM 550 to the cornea 115.

Figure 5G:
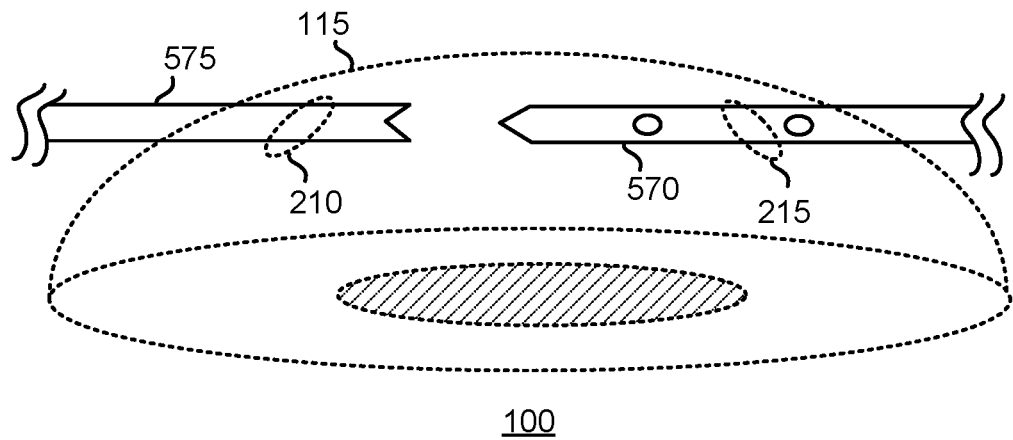
FIG. 5G shows an anterior chamber maintainer and another tool inserted into an eye according to one embodiment.

FIG. 5G shows an anterior chamber maintainer 570 and another tool 575 inserted into an eye 100 according to one embodiment. A physician inserts the ACM 570 through the first incision 215 in the cornea 115 and inserts the other tool 575 through the second incision 210. The physician can couple the ACM 570 to the other tool 575 inside the eye 100. For example, the distal tip of the ACM 570 can be physically keyed into or hooked onto the distal tip of the other tool 575. Once the ACM 570 is physically coupled to the other tool 575, the physician can manipulate the ACM 570 using the other tool 575. In particular, the physician positions the ACM 570 by removing the other tool from the second incision 210 such that the distal tip of the ACM 570 physically contacts the second incision 210. After fastening the ACM 570 to the second incision 210, the physician can uncouple the other tool 575 from the ACM 570.

Figure 5H:
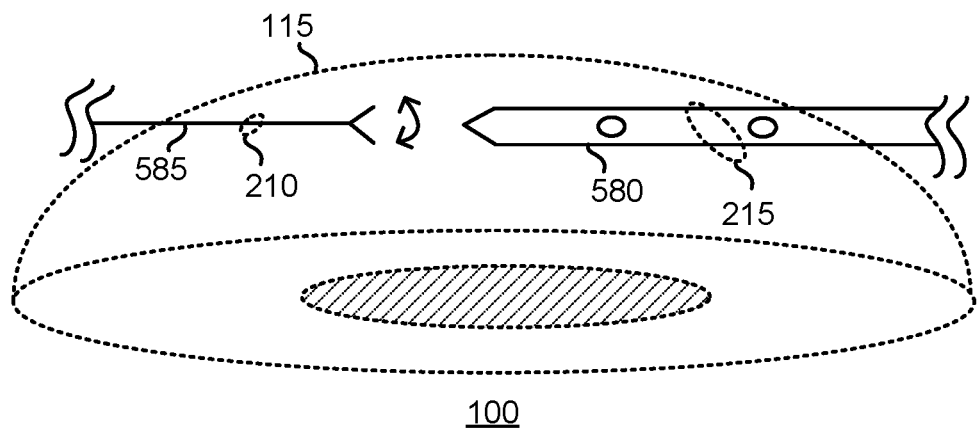
FIG. 5H shows an anterior chamber maintainer and a forceps tool inserted into an eye according to one embodiment.

FIG. 5H shows an anterior chamber maintainer 580 and a forceps tool 585 inserted into an eye 100 according to one embodiment. A physician inserts the ACM 580 through the first incision 215 in the cornea 115 and inserts the forceps tool 585 through the second incision 210. The physician can couple the ACM 570 to the forceps tool 585 inside the eye 100. In particular, pincers at the distal tip of the forceps tool 585 grab onto the distal tip of the ACM 570. Similar to the other tool 575 shown in FIG. 5G, the physician can use the forceps tool 585 to manipulate the ACM 570. Since the pincers can be folded into a compact form, the forceps tool 585 can have a smaller overall diameter than the ACM 570. Thus, a smaller forceps tool 585 can be advantageous because the physician can cut a smaller second incision 210 (relative to the first incision 215) to facilitate insertion of the forceps tool 585.

Figure 5I:
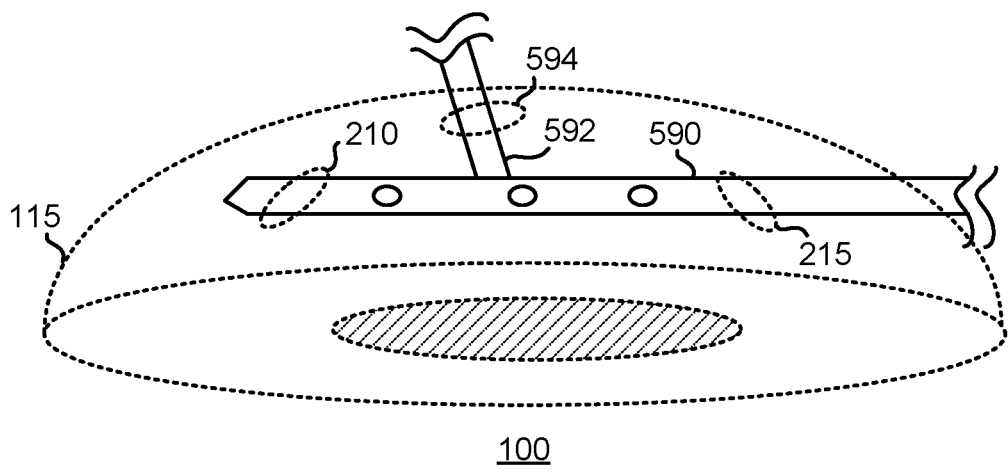
FIG. 5I shows an anterior chamber maintainer fastened to an eye at three points according to one embodiment.

FIG. 5I shows an anterior chamber maintainer 590 fastened to an eye 100 at three points according to one embodiment. The ACM 590 has an additional segment 592 inserted through a third incision 594 in the cornea 115. The segment 592 is movably coupled to the ACM 590. The ACM 590 and the segment 592 can be fastened to the incisions 210, 215, and 594 using any of the fasteners previously described. Though FIGS. 5A-H show embodiments of ACMs that are fastened to the cornea at two points, in practice, the ACM can be fastened to the cornea at two or more points, as illustrated in FIG. 5I. For example, to fasten the ACM 590 at four points of the cornea 115, the physician can insert a second additional segment through a fourth incision (not shown in FIG. 5I) in the cornea 115 that is also movably coupled to the ACM 590. Fastening the ACM 590 to additional points of the cornea 115 can be advantageous, e.g., because it provides more stability to prevent the ACM 590 from shifting around during surgery.

Example Prior Art Iris Retractor

Figure 6:
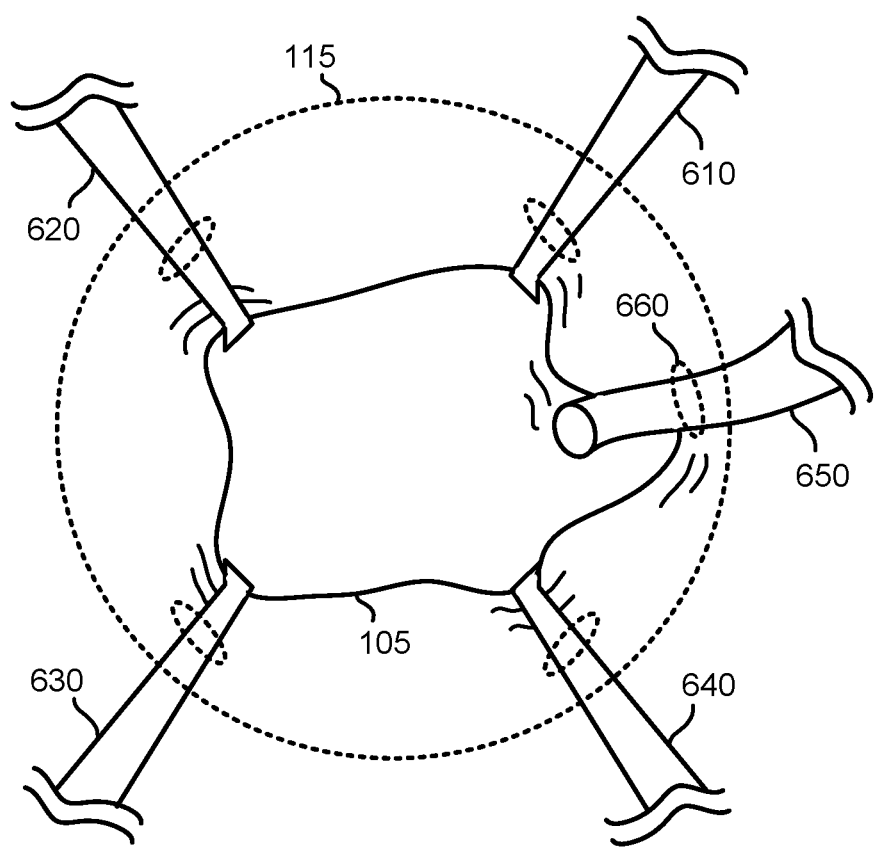
FIG. 6 shows a prior art iris retractor.

FIG. 6 shows a prior art iris retractor. An iris retractor (also referred to as an iris hook) is a surgical tool that can be used to manipulate the iris tissue of a patient's eye. During cataract surgery, a physician can dilate (e.g., using dilating agents such as mydriatic drops) the patient's eye to increase accessibility to cataracts in the patient's eye. When dilated, the patient's eye muscles and iris tissue contract, increasing the size of the pupil, which is the opening to the lens of the eye where cataracts may form. However, some patients do not dilate well and/or experience intraoperative floppy iris syndrome where a patient's iris does not successfully dilate pharmacologically (and/or is "floppy"). Thus, a physician can mechanically dilate the patient's iris by temporarily implanting iris retractors in the patient's eye.

In one example conventional method for pupil expansion and stabilization, a physician inserts four iris retractors 610, 620, 630, and 640 each through a different incision in the cornea 115. Each of the iris retractors hooks onto a portion of the iris 105. A challenge with existing iris retractors is that the iris can still shift or "flop," which interferes with other surgical tools during cataract surgery. For example, the iris 105 can interfere with a phaco tip 650 (or an ACM) or an incision 660 through which the phaco tip 650 is inserted. Iris wings can also be used to expand the iris, though the iris wings are not fastened to the cornea, and thus may become dislodged or shift around during surgery.

Example Iris Retractor Integrated with an Anterior Chamber Maintainer

Figure 7:
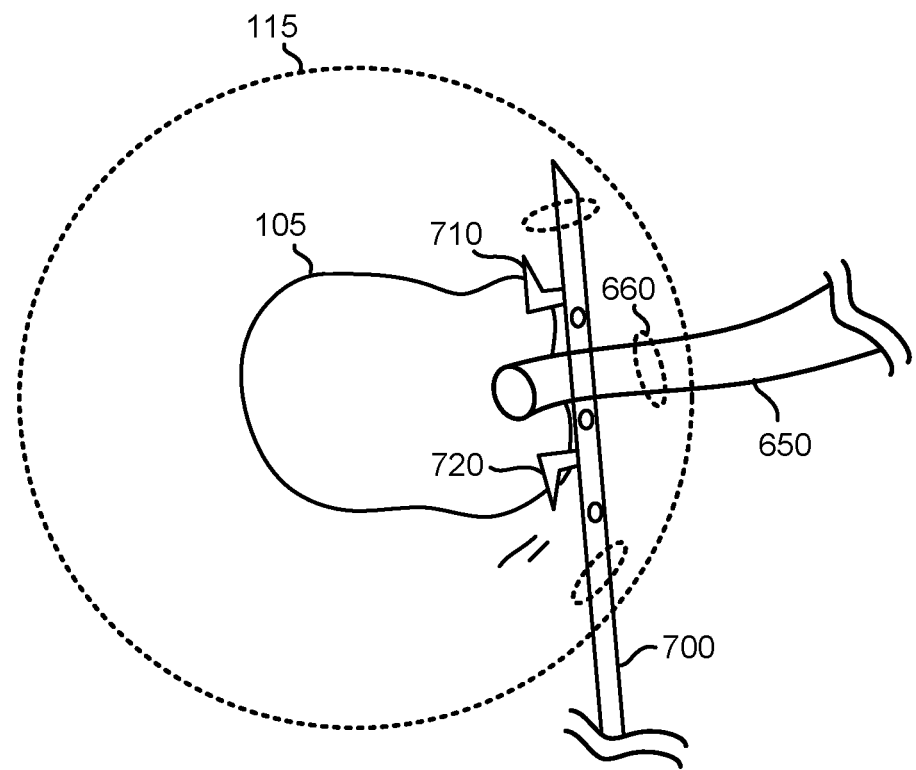
FIG. 7 shows an anterior chamber maintainer integrated with an iris retractor according to one embodiment.

FIG. 7 shows an anterior chamber maintainer 700 integrated with an iris retractor according to one embodiment. A physician inserts the ACM 700 through incisions in the cornea 115 and fastens the ACM 700 to the cornea 115. The ACM 700 includes one or more iris retractor hooks, e.g., iris retractor hooks 710 and 720. The iris retractor hooks physically attach to a portion of the iris 105. In some embodiments, the physician can use another iris retractor (not shown in FIG. 7) to attach a portion of a floppy iris to the iris retractor hooks, e.g., because the iris retractor hooks do not reach the portion of the floppy iris. Though two iris retractor hooks are shown in FIG. 7, in other embodiments, the ACM 700 may include different types of iris retractors with varying sizes and shapes (e.g., a curved hook or a hook with a beveled tip).

The physician can fasten the ACM 700 to a certain location in the eye (e.g., based on the location of two incisions in the cornea 115) such that the ACM 700 prevents the iris 115 from interfering with other surgical instruments. For example, in contrast with the prior art iris retractor shown in FIG. 6, the ACM 700 physically prevents the iris 105 from reaching the distal tip of the phaco tip 650 or the incision 660 through which the phaco tip 650 is inserted. Integrating the iris retractor hooks with the ACM 700 can also be advantageous because the physician does not need to use separate iris retractors and ACMs. Consolidating the iris retraction and irrigation solution functionality to a single surgical tool can reduce costs and reduce the number of incisions that the physician needs to cut in a patient's cornea. Though only one ACM is shown in FIG. 7, in practice, the physician can insert and fasten multiple ACMs to the patient's cornea for a surgery. For example, a first ACM attaches to the iris on the right side of the cornea and a second ACM attaches to the iris on the left side of the cornea. In some embodiments, the ACM 700 includes iris retractors without necessarily including a lumen and openings to provide irrigation solution.

In some embodiments, a physician uses the ACM 700 as a scaffolding structure that is coupled to other surgical instruments or devices, e.g., other types of iris retractors, irrigation sleeves, or aspiration nozzles. Thus, the other surgical instruments or devices are less likely to shift around inside the eye.

Figure 8:
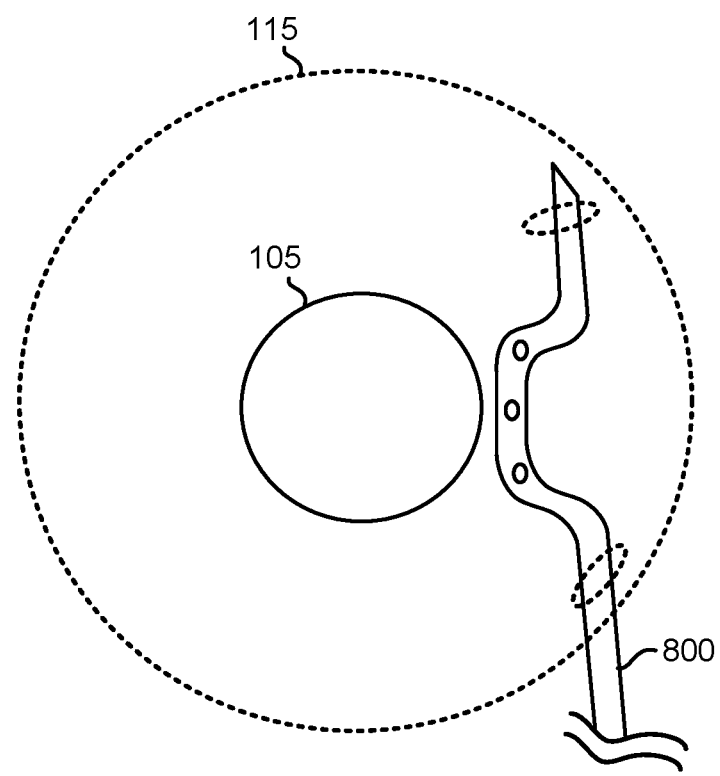
FIG. 8 shows an anterior chamber maintainer with curved segments according to one embodiment.

FIG. 8 shows an anterior chamber maintainer 800 with curved segments according to one embodiment. Curved segments may be advantageous, for example, because the ACM 800 can more closely conform to the anatomy of the eye (e.g., the curvature of the cornea 115) or can position the openings for providing irrigation solution closer toward the iris 105. In some embodiments, the ACM 800 includes one or more malleable segments. For instance, the malleable segments may be bent to facilitate insertion or positioning of the ACM 800 in the eye.

Example Fluidic Control System

Figure 9:
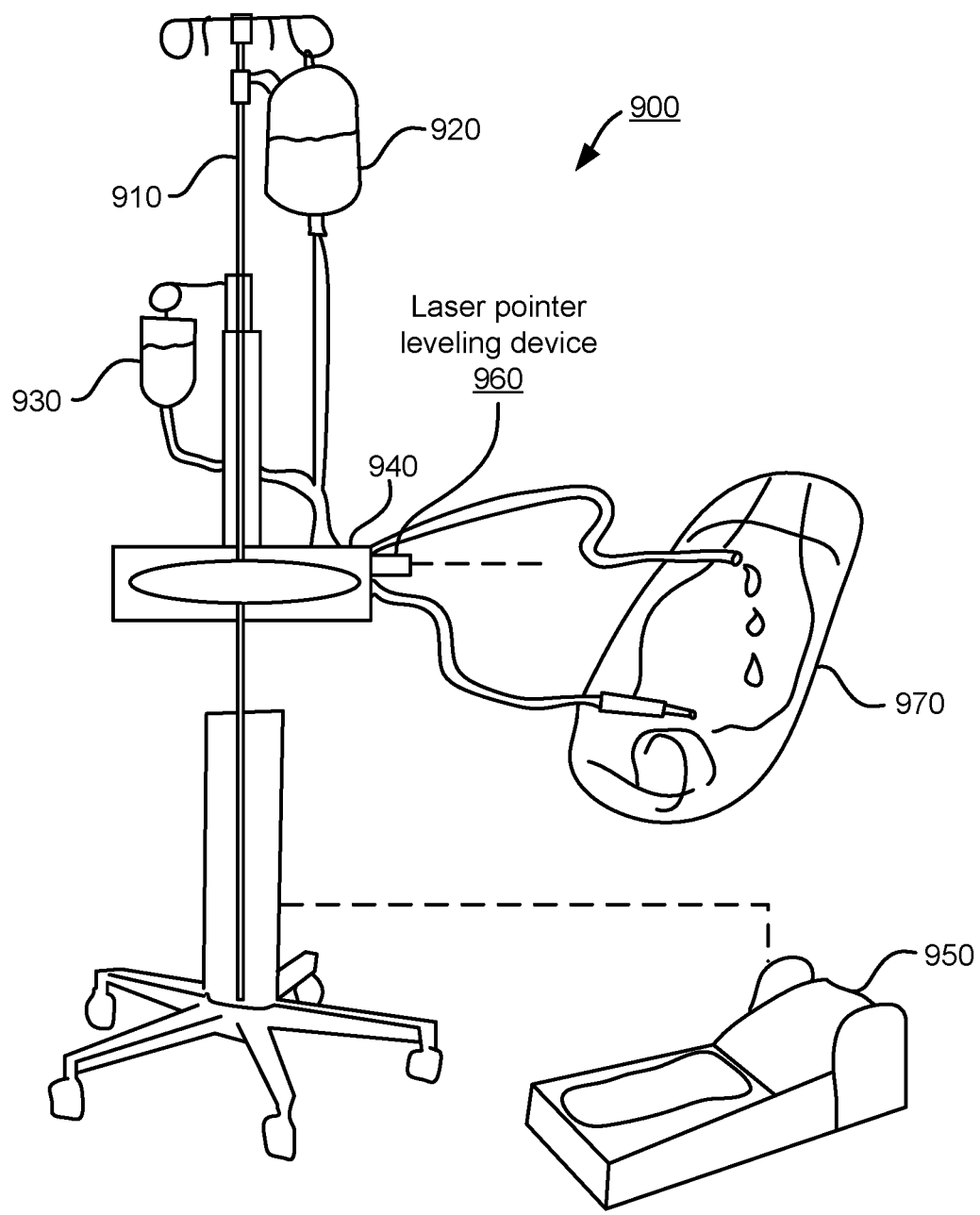
FIG. 9 shows a fluidic control system according to one embodiment.

FIG. 9 shows a fluidic control system 900 according to one embodiment. The fluidic control system 900, also referred to herein as the system 900, includes a stand 910, a first container 920, a second container 930, a fluid interface 940, a pedal 950, and optionally a laser 960, among other components. In one embodiment, the system 900 provides irrigation solution to a patient's eye 970 (e.g., the cornea of the eye in particular) during ocular surgery, for example, via an ACM according to any of the various embodiments described above.

The stand 910 is coupled to the first container 920 and the second container 930. In some embodiments, the system 900 may include more than two containers coupled to the stand 910. Each of the containers may be independently positioned at various heights along the stand 910. For example, the first container 920 is positioned at a height that is higher than the position of the second container 930. In some embodiments, the stand 910 includes two or more container holders to hold the containers. The container holders are movably coupled to the stand. For instance, the container holders slide along a rail of the stand and can be locked at a certain position using a braking mechanism. In one embodiment, the stand 910 includes a mechanism with an actuator (e.g., a motor) to automatically move the containers and/or container holders along the stand 910.

The first container 920 and the second container 930 are configured to hold fluids, liquids, or aqueous solutions such as an irrigation solution for ocular surgery. The containers may be an intravenous (IV) plastic bag, a metal type container, a glass type container, or any other suitable type of container for holding solutions. The containers may be coupled to surgical instruments such as a phaco tip or an ACM (e.g., as shown in embodiments of the previous figures) via tubing, valves, and/or other types of interfacing components, e.g., fittings, junctions, and/or the fluid interface 940 described below. In one embodiment, the second container 930 is positioned approximately 30-50 centimeters (22-37 mmHg) above the eye 970, and the first container 920 is positioned approximately 70-120 centimeters (51-88 mmHg) above the eye 970. In other embodiments, a physician can position the containers at any other heights above the eye 970 based on the physician's particular preferences. Since the containers are positioned at a height above the eye 970, solution from the containers can flow down toward the eye 970 due to gravitational force, e.g., thus not requiring the use of another actuator such as a fluid pump. In some embodiments, the containers may be compressed at two or more different pressures for systems that do not base the fluid flow and/or pressure of the solution by gravity.

The fluid interface 940 is coupled to two or more containers, e.g., the first container 920 and the second container 930 via tubing. The fluid interface 940 may include a one-way valve to prevent high pressure solution of the first container 920 from entering the second container 930. In one embodiment, the fluid interface 940 is coupled to surgical instruments (e.g., an ACM) via additional tubing. The fluid interface 940 controls whether solution from the first container 920 and/or the second container 930 is provided to the corresponding tubing for delivery to a surgical site, e.g., the eye 970. For instance, the fluid interface 940 opens a first valve and/or a second valve to pass solution through tubing to a surgical tool (e.g., an ACM) from the first container 920 and/or the second container 930, respectively. The fluid interface 940 can provide a continuous flow of solution from the first container 920 and/or the second container 930. The fluid interface 940 may open or close the valves based on an input signal from an input device such as the pedal 950.

The pedal 950 is communicatively coupled to the stand 910. In one embodiment, the pedal includes a lever that may be adjusted to two or more positions. For example, the pedal is placed on the ground and a physician adjusts the position of the lever by stepping on the pedal. During surgery, if the physician wants to deliver solution at a low pressure to manipulate fragments (and/or maintain the shape of the anterior chamber of the eye 970 using an ACM), the physician presses the pedal to move the lever to a first position corresponding to the second container 930 (lower than the first container 920). Accordingly, the pedal 950 provides a first input signal to the fluid interface 940. In response to receiving the first input signal, the fluid interface 940 provides a solution at the low pressure from the second container 930 via a surgical tool (e.g., a phaco tip or ACM) inserted into the cornea of the eye 970. Additionally, if the physician wants to aspirate fragments using solution at a high pressure (relative to the low pressure), the physician presses the pedal to move the lever to a second position corresponding to the second container 930, e.g., the physician presses the pedal further down. Accordingly, the pedal 950 provides a second input signal to the fluid interface 940. In response to receiving the second input signal, the fluid interface 940 provides a solution at the high pressure from the first container 920 to the surgical tool (e.g., a phaco tip or ACM). In other embodiments, instead of a pedal, the system 900 includes any other suitable type of input device (e.g., a joystick, mouse, keyboard, button, etc.) for providing input signals to the fluid interface 940.

In one embodiment, the system 900 includes two or more pedals (or input devices), each corresponding to a container. The fluid interface 940 provides solution from a container in response to receiving an input signal from the corresponding pedal.

In some embodiments, a laser 960 is coupled to the stand 910. A physician can use the laser 960 to visually align the containers (or any other reference point on the stand 910) to the patient's eye 970 to prepare for a surgical procedure. By using an accurate alignment of the containers relative to the eye 970, the system 900 can provide more granularity and control regarding the pressure of the solution provided to the eye 970. Thus, the flow rate of the solution provided by the system 900 will be more accurate and consistent during surgery. In some embodiments, instead of a laser 960, the system 900 may include any other suitable type of alignment device such as a lighted pointer or a mechanical visual guide.

In one embodiment, the system 900 includes one container coupled to the stand 910 instead of two or more separate containers. The container includes two or more chambers (e.g., sub-containers) each having a compression level and containing solution. For example, the container includes a first chamber having a low compression level and a second chamber having a high compression level, relative to the low compression level. In some embodiments, the chambers or sub-containers may be at a same height. The fluid interface 940 delivers solution from the chambers based on input signals from an input device. For example, the fluid interface 940 delivers solution from the first chamber in response to the physician pressing the pedal 950 to a first position, and delivers solution from the second chamber in response to the physician pressing the pedal 950 to a second position. Since the system 900 includes both high and low pressure solutions, the system 900 can quickly—almost instantaneously—switch between providing one of the two (or more) solutions. Thus, as an example, the physician can deliver low pressure solution for the majority of a surgery and only switch to high pressure solution for a certain period of time when it is needed for the surgery.

ALTERNATIVE CONSIDERATIONS

Upon reading this disclosure, those of skill in the art will appreciate still additional alternative structural and functional designs through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the apparatus disclosed herein without departing from the spirit and scope defined in the appended claims. Features such as sharp tips (e.g., shown in FIGS. 2B-D), needles (e.g., shown in FIGS. 3B-D), different types of openings (e.g., shown in FIGS. 4A-D), different types of fasteners (e.g., shown in FIGS. 5A-I), and integrated iris retractors (e.g., shown in FIG. 7) may be used in any of the anterior chamber maintainer embodiments or designs described herein. In some embodiments, an ACM may include integrated iris retractors without necessarily including openings (or a lumen) for irrigation solution.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present). In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

What is claimed is:

1. A method for using an anterior chamber maintainer, the method comprising:
   cutting a first incision at a location of a cornea of an eye;
   cutting a second incision at a different location of the cornea;
   cutting a third incision at another different location of the cornea;
   inserting the anterior chamber maintainer through the first incision, the anterior chamber maintainer being a tubular structure including a first section, second section, and third section adjacent to the first section and the second section;
   fastening the first section to the first incision;
   fastening the second section to the second incision such that at least a first opening directed in a first direction a second opening directed in a second direction in the third section are positioned inside the eye, wherein the first direction is different than the second direction;
   fastening the anterior chamber maintainer to the third incision;
   directing fluid in the first direction through the first opening into the eye; and
   directing fluid in the second direction through the second opening into the eye.

2. The method of claim 1, wherein inserting the anterior chamber maintainer through the first incision comprises using a sharp edge positioned in vicinity of the first section.

3. The method of claim 1, wherein fastening the first section to the first incision or fastening the second section to the second incision comprises:
   using a friction surface having a higher coefficient of friction than another coefficient of friction of a surface of the third section.

4. The method of claim 1, wherein fastening the first section to the first incision or fastening the second section to the second incision comprises:

using a magnet coupled to the first section or the second section.

5. The method of claim 1, wherein fastening the first section to the first incision or fastening the second section to the second incision comprises:
using a plurality of ridges that physically contacts the first incision or the second incision.

6. The method of claim 1, further comprising:
inserting a tool into the eye; and
manipulating the tool to position the anterior chamber maintainer.

7. The method of claim 6, wherein the tool is a needle, and wherein the method further comprises:
inserting the needle through the first incision, wherein the needle is positioned inside the tubular structure of the anterior chamber maintainer; and
removing the needle from the tubular structure after the anterior chamber maintainer is positioned.

8. The method of claim 1, further comprising:
coupling the anterior chamber maintainer to a fluidic control system to receive the fluid at a plurality of different fluid pressures; and
selecting one of the plurality of different fluid pressures at which to provide the fluid into the eye.

9. The method of claim 1, further comprising:
fastening one or more iris retractors of the anterior chamber maintainer to a portion of an iris tissue of the eye.

10. The method of claim 6, further comprising:
manipulating another tool in the eye while providing the fluid into the eye.

11. A method for using an anterior chamber maintainer, the method comprising:
cutting a first incision at a location of a cornea of an eye;
cutting a second incision at a different location of the cornea;
inserting the anterior chamber maintainer through the first incision, the anterior chamber maintainer being a tubular structure including a first section, second section, and third section adjacent to the first section and the second section;
fastening the first section to the first incision;
fastening the second section to the second incision such that at least a first opening directed in a first direction a second opening directed in a second direction in the third section are positioned inside the eye, wherein the first direction is different than the second direction;
inserting a tool into the eye;
manipulating the tool to position the anterior chamber maintainer;
directing fluid in the first direction through the first opening into the eye;
directing fluid in the second direction through the second opening into the eye; and
manipulating another tool in the eye while providing the fluid into the eye.

12. The method of claim 11, wherein inserting the anterior chamber maintainer through the first incision comprises using a sharp edge positioned in vicinity of the first section.

13. The method of claim 11, wherein fastening the first section to the first incision or fastening the second section to the second incision comprises:
using a friction surface having a higher coefficient of friction than another coefficient of friction of a surface of the third section.

14. The method of claim 11, wherein the tool is a needle, and wherein the method further comprises:
inserting the needle through the first incision, wherein the needle is positioned inside the tubular structure of the anterior chamber maintainer; and
removing the needle from the tubular structure after the anterior chamber maintainer is positioned.

15. The method of claim 11, further comprising:
cutting a third incision at another different location of the cornea; and
fastening the anterior chamber maintainer to the third incision.

16. The method of claim 11, further comprising:
coupling the anterior chamber maintainer to a fluidic control system to receive the fluid at a plurality of different fluid pressures; and
selecting one of the plurality of different fluid pressures at which to provide the fluid into the eye.

17. The method of claim 11, further comprising:
fastening one or more iris retractors of the anterior chamber maintainer to a portion of an iris tissue of the eye.

* * * * *